US009665949B2

(12) United States Patent
Kikuchi et al.

(10) Patent No.: US 9,665,949 B2
(45) Date of Patent: May 30, 2017

(54) SKIN DULLNESS EVALUATION APPARATUS AND SKIN DULLNESS EVALUATION METHOD

(71) Applicant: SHISEIDO COMPANY, LTD., Tokyo (JP)

(72) Inventors: Kumiko Kikuchi, Kanagawa (JP); Yuji Masuda, Kanagawa (JP)

(73) Assignee: SHISEIDO COMPANY, LTD., Tokyo (JP)

(*) Notice: Subject to any disclaimer, the term of this patent is extended or adjusted under 35 U.S.C. 154(b) by 0 days.

(21) Appl. No.: 14/783,159

(22) PCT Filed: Mar. 24, 2014

(86) PCT No.: PCT/JP2014/058106
§ 371 (c)(1),
(2) Date: Oct. 8, 2015

(87) PCT Pub. No.: WO2014/174962
PCT Pub. Date: Oct. 30, 2014

(65) Prior Publication Data
US 2016/0035109 A1     Feb. 4, 2016

(30) Foreign Application Priority Data

Apr. 26, 2013   (JP) .................................. 2013-094131

(51) Int. Cl.
*G06K 9/00* (2006.01)
*G06T 7/90* (2017.01)
(Continued)

(52) U.S. Cl.
CPC .............. *G06T 7/90* (2017.01); *A61B 5/1032* (2013.01); *A61B 5/441* (2013.01); *G06K 9/4652* (2013.01);
(Continued)

(58) Field of Classification Search
CPC .... A61B 5/1032; A61B 5/441; G06K 9/4652; G06K 2009/4666; G06T 2207/30088; G06T 7/0012; G06T 7/408
(Continued)

(56) References Cited

U.S. PATENT DOCUMENTS 8,094,186 B2 *  1/2012  Fukuoka ................ A61B 5/442
                                                    348/77
8,358,348 B2    1/2013  Mohammadi et al.
(Continued)

FOREIGN PATENT DOCUMENTS

JP    H11-299743    11/1999
JP    2000-201899    7/2000
(Continued)

OTHER PUBLICATIONS

Kikuchi et al., May 2015, "Image analysis of skin color heterogeneity focusing on skin chromophores and the age-related changes in facial skin", retrieved from internet on Nov. 9, 2015 at <https://www.ncbi.nlm.nih.gov/pubmed/25130270.*
(Continued)

*Primary Examiner* — Gregory F Cunningham
(74) *Attorney, Agent, or Firm* — IPUSA, PLLC

(57) ABSTRACT

A skin dullness evaluation apparatus includes a frequency analyzing unit that decomposes a skin image into color heterogeneity of a predetermined size; a color heterogeneity index obtaining unit that obtains color data of skin from each of the color heterogeneity decomposed by the frequency analyzing unit, and obtains a color heterogeneity index of the color heterogeneity from the obtained color data of skin; and a dullness evaluation unit that evaluates skin dullness corresponding to the skin image based on the color heterogeneity index obtained by the color heterogeneity index obtaining unit.

15 Claims, 13 Drawing Sheets

(51) Int. Cl.
*A61B 5/103* (2006.01)
*A61B 5/00* (2006.01)
*G06K 9/46* (2006.01)
*G06T 7/00* (2017.01)

(52) U.S. Cl.
CPC .... *G06T 7/0012* (2013.01); *G06K 2009/4666* (2013.01); *G06T 2207/30088* (2013.01)

(58) Field of Classification Search
USPC ........................................................ 382/128
See application file for complete search history.

(56) References Cited

U.S. PATENT DOCUMENTS

| 2011/0142305 | A1 | 6/2011 | Jiang et al. | |
|---|---|---|---|---|
| 2016/0166194 | A1* | 6/2016 | Gareau | A61B 5/6898 600/328 |

FOREIGN PATENT DOCUMENTS

| JP | 2000201899 | A | * | 7/2000 | ............. G01N 33/50 |
|---|---|---|---|---|---|
| JP | 2000-350702 | | | 12/2000 | |
| JP | 2002-102177 | | | 4/2002 | |
| JP | 2002102177 | A | * | 4/2002 | ............... A61B 5/00 |
| JP | 2010-046309 | | | 3/2010 | |
| JP | 2010-048612 | | | 3/2010 | |
| JP | 2010046309 | A | * | 3/2010 | ............... A61B 5/00 |
| JP | 2010048612 | A | * | 3/2010 | ............. G01N 33/50 |
| JP | 2011-118671 | | | 6/2011 | |
| JP | 2011118671 | A | * | 6/2011 | ............... G06T 1/00 |
| JP | 2011-240086 | | | 12/2011 | |
| JP | 2011240086 | A | * | 12/2011 | ............. A61B 5/107 |
| JP | 2013-043017 | | | 3/2013 | |

OTHER PUBLICATIONS

Yayoi Inoue et al., "Study of skin color unevenness using independent component analysis", Journal of SCCJ, vol. 45, No. 3, : Sep. 2011 (Sep. 20, 2011), p. 218 to 224.*
Osamu Kaneko et al., Measuring Apparent Darkening of the Skin (First Report) Factors Inherent in Light Reflected from the Skin, J. Soc. Cosmet. Chem. Japan., vol. 31, No. 1 (1997), pp. 44-51.
Osamu Kaneko et al., Measuring Apparent Darkening of the Skin (Second Report) Relationship between Age-Associated Changes in Physical Properties of the Skin and Apparent Darkening, J. Soc. Cosmet. Chem. Japan., vol. 31, No. 4 (1997), pp. 429-438.
Yayoi Inoue et al., Study of skin color unevenness using independent component analysis, Journal of SCCJ, vol. 45, No. 3, Sep. 20, 2011 (Sep. 20, 2011), pp. 218-224.
International Search Report mailed on May 13, 2014.
Extended European Search Report mailed Dec. 5, 2016.
Taiwanese Office Action mailed Feb. 23, 2017.

* cited by examiner (B)

(A)

SKIN DULLNESS EVALUATION APPARATUS AND SKIN DULLNESS EVALUATION METHOD

BACKGROUND OF THE INVENTION

1. Field of the Invention

The present invention relates to a skin dullness evaluation apparatus and a skin dullness evaluation method.

2. Description of the Related Art

Skin dullness is a specific phenomenon and it is said that the skin dullness is a condition or the like that occurs at the entirety of face or a portion such as around eyes, at a cheek or the like, in which redness of skin decreases and yellowish of skin increases, in which "glow" or transparency of shin decreases, in which brightness decreases and becomes dark due to shadow by concavo-convex or the like at a skin surface. Further, it is said that a generation factor of the dullness is lowering of redness of skin color due to poor blood circulation, deposition of diffuse melanin, shadow by concavo-convex at a skin surface that occurs due to lowering of resilience of shin, lowering of transparency (optical transparency) due to thickening of skin or the like, lowering of glow due to diffusion at a skin surface, yellowing of skin in accordance with ageing or the like.

A method is known in which such skin dullness is digitized by micro concavo-convex degree of a skin surface, or skin spectrotransparency in addition to by coloring degree due to a quantity of melanin, or good, or bad in blood flow or blood circulation, for example (see Non-patent Documents 1, 2, for example).

[Patent Documents]
[Patent Document 1]Japanese Patent No. 3,798,550
[Patent Document 2]Japanese Patent No. 3,727,807
[Patent Document 3]Japanese Laid-open Patent Publication No. 2011-240086
[Non-patent Documents]
[Non-patent Document 1] Osamu Kaneko, Hiroyuki Tsukada, Yoshie Ishikawa, Yukiko Kawaguchi; J. Soc, Cosmet. Chem. Japan.; Vol. 31, No. 1 (1997)
[Non-patent Document 2] Osamu Kaneko, Yukiko Kawaguchi, Yoshie Ishikawa, Kazomasa Inagaki; J. Soc, Cosmet, Chem, Japan.; Vol. 31, No. 4 (1997)

However, the influence of color heterogeneity (unevenness of color), that are said to be caused by redness of cheek, freckles, acne scars or the like, for example, has not been specifically considered on the definition of the above described conventional skin dullness. On the other hand, according to the research or survey conducted by the present applicant, a result was obtained that subjects who care (have) the skin dullness also care (have) color heterogeneity.

SUMMARY OF THE INVENTION

The present invention is made in light of the above problems, and provides a technique to appropriately evaluate skin dullness using color heterogeneity.

According to an embodiment, there is provided a skin dullness evaluation apparatus including a frequency analyzing unit that decomposes a skin image into color heterogeneity of a predetermined size; a color heterogeneity index obtaining unit that obtains color data of skin from each of the color heterogeneity decomposed by the frequency analysing unit, and obtains a color heterogeneity index of the color heterogeneity from the obtained color data of skin; and a dullness evaluation unit that evaluates skin dullness corresponding to the skin image based on the color heterogeneity index obtained by the color heterogeneity index obtaining unit.

DETAILED DESCRIPTION OF THE PREFERRED EMBODIMENTS

The invention will be described herein with reference to illustrative embodiments. Those skilled in the art will recognize that many alternative embodiments can be accomplished using the teachings of the present invention and that the invention is not limited to the embodiments illustrated for explanatory purposes.

(Analyzing Apparatus of Color Heterogeneity of Skin: Example of Functional Structure)

Figure 1:
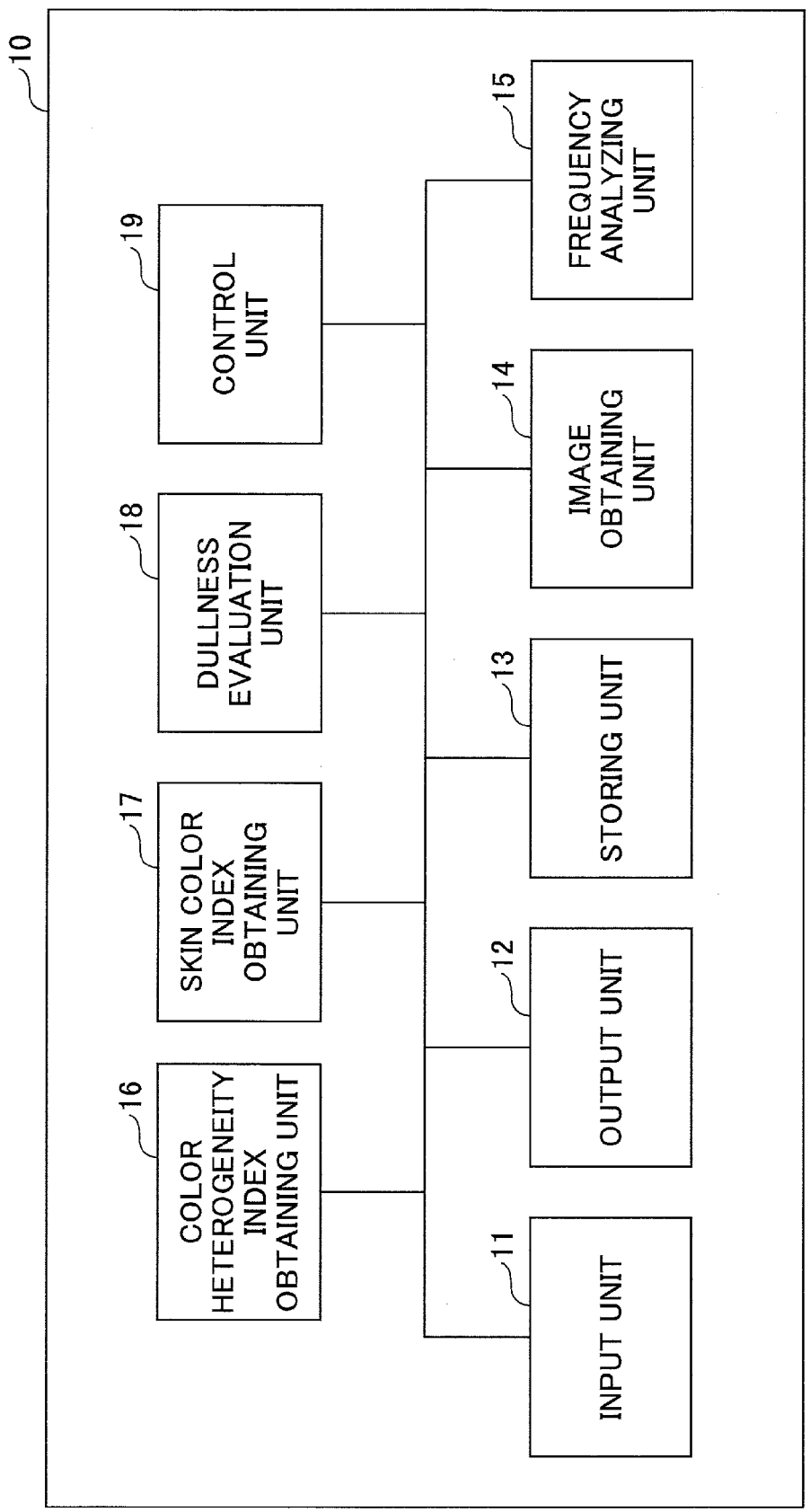
FIG. 1 is a view illustrating an example of a functional structure of a skin dullness evaluation apparatus of an embodiment.

FIG. 1 illustrates an example of a functional structure of a skin dullness evaluation, apparatus of the embodiment. As illustrated in FIG. 1, a skin dullness evaluation apparatus 10 includes an input unit 11, an output unit 12, a storing unit 13, an image obtaining unit 14, a frequency analyzing unit 15, a color heterogeneity index obtaining unit 16, a skin color index obtaining unit 17, a dullness evaluation unit 18 and a control unit 19.

The skin dullness evaluation apparatus 10 decomposes a skin image into color heterogeneity of a predetermined size, obtains color data of skin from the decomposed color heterogeneity, obtains a color heterogeneity index from the obtained color data of skin, and evaluates skin dullness corresponding to the skin image based on the obtained color heterogeneity index, for example.

The input unit 11 accepts an input of starting/ending, setting or the like of various instructions regarding a skin dullness evaluation process from a user or the like that uses the skin dullness evaluation apparatus 10, for example. The input unit 11 is a pointing device such as a keyboard, a mouse or the like, for a general purpose computer such as a PC (Personal Computer) or the like, for example. The input unit 11 may be an audio input device such as a microphone or the like capable of inputting the above described input by voice or the like, for example.

The output unit 12 outputs the content input by the input unit 11, a content executed based on the input content or the like. Here, the output unit 12 is a display, a speaker or the like, for example. The output unit 12 may include a printing device such as a printer or the like, Here, when the skin dullness evaluation apparatus 10 is a smartphone, a tablet terminal or the like, for example, the above described input unit 11 and the output unit 12 may have a structure in which input and output are integrally configured such as a touch panel, for example.

The storing unit 13 stores various data necessary in this embodiment. Specifically, the storing unit 13 stores various programs, various setting data or the like for executing the skin dullness evaluation process of the embodiment. The storing unit 13 stores a skin image in which the entirety of a cheek of a subject is photographed, a color heterogeneity index, a skin color index, a dullness index, or a dullness judgment value corresponding to the skin image, or the like, for example.

Here, the storing unit 13 may be an aggregation of the above described various data, and may have a function as a database that is systematically configured such that data can be searched and extracted using a keyword or the like, for example. Further, data stored in the storing unit 13 may be obtained from an external apparatus via a communication network, for example.

The image obtaining unit 14 obtains a skin image in which skin of a portion at which the subject feels existence of dullness is photographed by a SIA system (Skin Image Analyzer) or the like that is configured by a diffused illumination box and a digital camera, for example. Here, for the photographed image, it is possible to suppress reflection at a skin surface, the influence of shadow or the like by irradiating diffuse light, and it is possible to obtain color data of skin by measuring "color" of the skin.

The frequency analyzing unit 15 decomposes the skin image obtained by the image obtaining unit 14 into color heterogeneity of a predetermined size by a band-pass filter or the like having a predetermined frequency. The frequency analyzing unit 15 may decompose the skin image into color heterogeneity each of which is less than or equal to 4 mm, for example.

The color heterogeneity index obtaining unit 16 obtains color data of skin from the color heterogeneity that are decomposed into the predetermined size by the frequency analysing unit 15, and obtains the color heterogeneity index from the obtained color data of skin. Here, the color data of skin is an RGB value in an RGB color system, an XYZ value in an XYZ color system converted from the RGB color system of the photographed skin, image, for example.

The color heterogeneity index obtaining unit 16 may obtain the color heterogeneity index based on distribution of a pigment composition such as a melanin component or the like obtained from the color data of skin. The color heterogeneity index obtaining unit 16 may decompose into a melanin component and a hemoglobin component in skin and obtain a component amount for each of them using a method disclosed in Japanese Patent No. 3,798,550 by the present applicant, for example. In other words, the color heterogeneity index obtaining unit 16 obtains the component amount of the melanin component or the like in the skin by performing a multiple regression analysis using a reflection spectrum of skin, an absorbance model obtained by substituting transmittance in Lambert-Beer law by reflectance of skin and an absorption constant spectrum of components of skin, for example.

Further, the color heterogeneity index obtaining unit 16 may obtain the component amount of the melanin component or the like in skin using a method disclosed in Japanese Patent No. 3,727,807 by the present applicant. In other words, the color heterogeneity index obtaining unit 16 may previously obtain a multiple regression formula by performing a multiple regression analysis of data of a measured color value of skin and a component amount of the melanin component or the like in skin, and obtain the component amount of the melanin component or the like in skin from the measured color value using the multiple regression formula, for example.

The color heterogeneity index obtaining unit 16, by generating an image that indicates density of the predetermined pigment composition obtained by the above described method and its distribution, multiplies a density value greater than or equal to a density average value and the number of pixels each of which having the density value greater than or equal to the density average value, integrates it, and digitizes the color heterogeneity to obtain the color heterogeneity index.

The skin color index obtaining unit 17 obtains the skin color index based on the color data of skin obtained by measuring the skin image obtained by the image obtaining unit 14, or a skin portion corresponding to the skin image. The skin color index obtaining unit 17 obtains, as the skin color index, a "pigmentation index" based on the component amount of the melanin component, a "congestion condition index" based on hemoglobin oxygen saturation, a "dullness color heterogeneity index" based on a color heterogeneity index obtained by the color heterogeneity index obtaining unit 16 or the like, for example.

The dullness evaluation unit 18 evaluates the skin dullness corresponding to the skin image based on the color heterogeneity index obtained by the color heterogeneity index obtaining unit 16. Here, the dullness evaluation unit 18 may evaluate the skin dullness for each index that influences the shin color based on the respective skin color index obtained by the skin color index obtaining unit 17. Further, the dullness evaluation unit 18 may totally evaluate the skin dullness corresponding to the skin, image based on a skin dullness index obtained by performing a multiple regression analysis using the skin color indexes.

The control unit 19 controls the entirety of the components of the skin dullness evaluation apparatus 10. The control unit 19 controls at least one of obtaining the color heterogeneity index, obtaining the skin color index, obtaining the dullness index, performing the skin dullness evaluation process or the like, for example, (Skin Dullness Evaluation Apparatus: Hardware Structure)

Here, an execution program (skin dullness evaluation program) is generated for having a computer execute each of the functions of the skin dullness evaluation apparatus 10 as described above, and is installed in a general purpose PC, a server or the like, for example, With this, it is possible to actualize the skin dullness evaluation process or the like of the embodiment.

Figure 2:
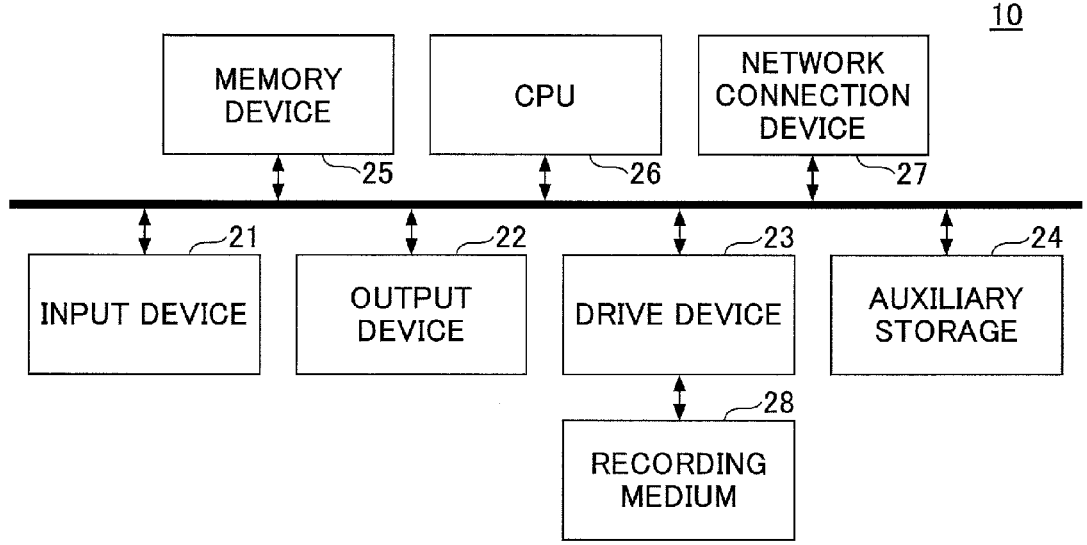
FIG. 2 is a view illustrating an example of a hardware structure capable of performing a skin dullness evaluation process.

FIG. 2 is a view illustrating an example of a hardware structure capable of executing the skin dullness evaluation process. The computer main body illustrated in FIG. 2 is configured to include an input device 21, an output device 22, a drive device 23, an auxiliary storage 24, a memory device 25, a CPU (Central Processing Unit) 26 that performs various controls and a network connection device 27, and these are connected with each other by a system bus B.

The input device 21 includes a pointing device such as a keyboard, a mouse or the like, an audio input device such as a microphone or the like that is operated by a user or the like, and inputs various operation signals such as an instruction to execute a program or the like from the user or the like. Further, the input device 21 includes an input unit that inputs a skin image of a subject that is photographed using a diffused illumination box, a digital camera and the like, for example.

The output device 22 includes a display that displays various windows, data or the like necessary for operating the computer main body that performs the processes of the embodiment, and displays execution processes, results or the like by a control program included in the CPU 26.

Here, the execution program that is installed in the computer main body of the embodiment may be provided by a portable recording medium 28 or the like such as a USB (Universal Serial Bus) memory, a CD-ROM or the like, for example. The recording medium 28 is capable of being set in the drive device 23, and the execution program included in the recording medium 28 is installed in the auxiliary storage 24 from the recording medium 28 via the drive device 23.

The auxiliary storage 24 is a storage unit such as a hard disk or the like, and stores the execution program of the embodiment, a control program provided in the computer or the like, and is capable of inputting and outputting data in accordance with necessity.

The memory device 25 stores the execution program or the like that is read out by the CPU 26 from the auxiliary storage 24. Here, the memory device 25 is a ROM (Read Only Memory), a RAM (Random Access Memory) or the like. Here, the above described auxiliary storage 24 and the memory device 25 may be integrally structured as a single storing device.

The CPU 26 actualizes the skin dullness evaluation process of the embodiment by controlling the entirety of the processes of the computer such as various calculation, input and output between each of the hardware structure units or the like, based on the control program such as an OS (Operating System) or the like, and the execution program stored in the memory device 25. Here, the various data or the like that are necessary when executing the program may be obtained from the auxiliary storage 24 and the executed result or the like may be stored therein.

The network connection device 27 obtains the execution program from another apparatus or the like that is connected to a communication network or the like typically the Internet, LAN (Local Area Network) or the like by connecting to the communication network or the like. Further, it is possible for the network connection device 27 to provide the executed result obtained by executing the program or the execution program itself of the embodiment to another apparatus or the like.

According to the hardware structure as described above, it is possible to perform the skin dullness evaluation process of the embodiment. Further, the skin dullness evaluation process of the embodiment can be easily actualized, by a general purpose PC or the like by installing the execution program.

(Relationship Between Skin Dullness and Color Heterogeneity)

Here, a relationship between the skin dullness and color heterogeneity is explained. As described above, conventionally, the influence of color heterogeneity has not been specifically considered for on the definition of the skin dullness. However, according to the researched result of the present applicant, the influence of the color heterogeneity are indicated for the skin dullness.

Figure 3:
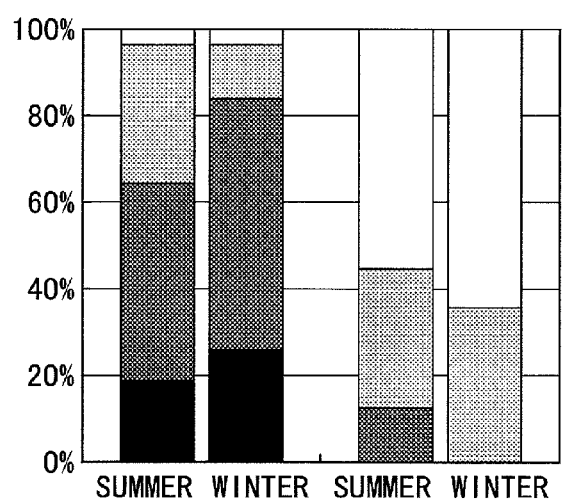
FIG. 3 is a view illustrating a result of an attitude survey on color heterogeneity regarding the skin dullness.

FIG. 3 is a view illustrating a result of an attitude survey on color heterogeneity regarding the skin dullness. In the survey of FIG. 3, the result is illustrated in which whether each subject feels existence of color heterogeneity is researched, targeting healthy females from 35 to fifties including 31 subjects who answered "feeling existence of skin dullness" and 31 subjects who answered "having transparency on skin" by self-assessment, during each period of summer and winter.

As illustrated in FIG. 3, for the subjects who answered "feeling existence of dullness (with dullness)", the number of the subjects who feel existence of "color heterogeneity" is large, while for the subjects who answered "having transparency on skin (with transparency)", the number of the subjects who don't feel existence of "color heterogeneity" is large. As such, the survey of FIG. 3 indicates that the subjects who answered as feeling existence of the skin dullness also feel existence of color heterogeneity at the same time.

Figure 4:
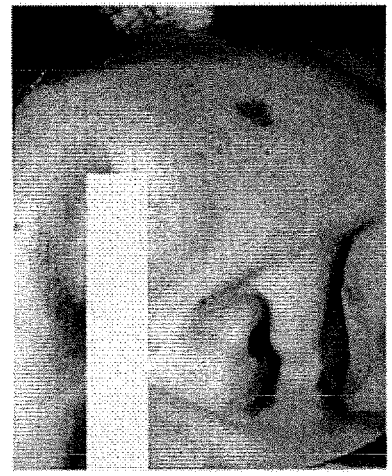
FIG. 4 is a view illustrating an example of a visual evaluation on skin images.
Figure 4:
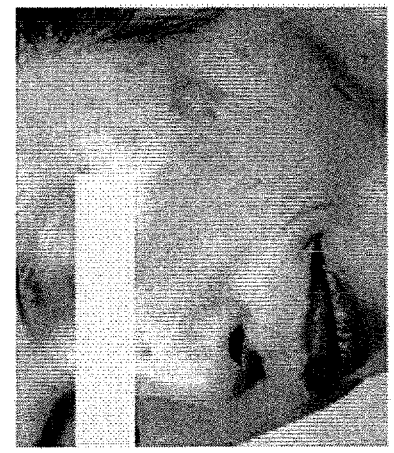
Figure 4:
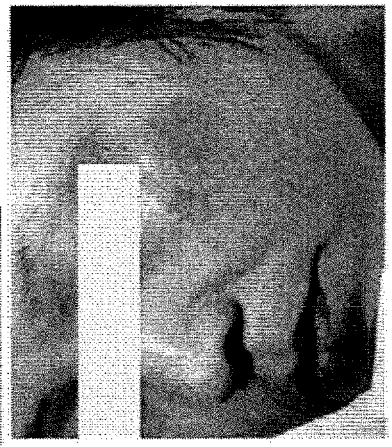
Figure 4:
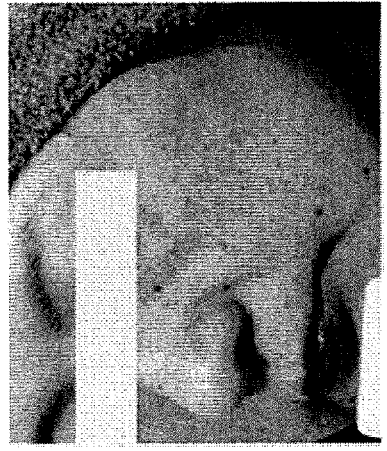

FIG. 4-(A) and FIG. 4-(B) are views illustrating an example of a visual evaluation on skin images. FIG. 4-(A) and FIG. 4(B) illustrate examples in which an experienced sensory evaluator (panelist) performs a visual evaluation whether the sensory evaluator feels existence of the skin dullness for each of the skin images.

According to the visual evaluation by the sensory evaluator, the skin images illustrated in FIG. 4-(A) are evaluated to feel existence of the skin dullness, while the skin images illustrated in FIG. 4-(B) are evaluated to feel existence of skin freckle. Here, by comparing FIG. 4-(A) and FIG. 4-(B), the size of the color heterogeneity of the subjects of FIG. 4-(A) is smaller than the size of the color heterogeneity of the subjects of FIG. 4-(B).

As such, for the examples that are evaluated to feel existence of the skin dullness by the visual evaluation, the size of the color heterogeneity is small and thus it is indicated that the size of the color heterogeneity influences on the skin dullness.

(Color Heterogeneity Index)

Figure 5:
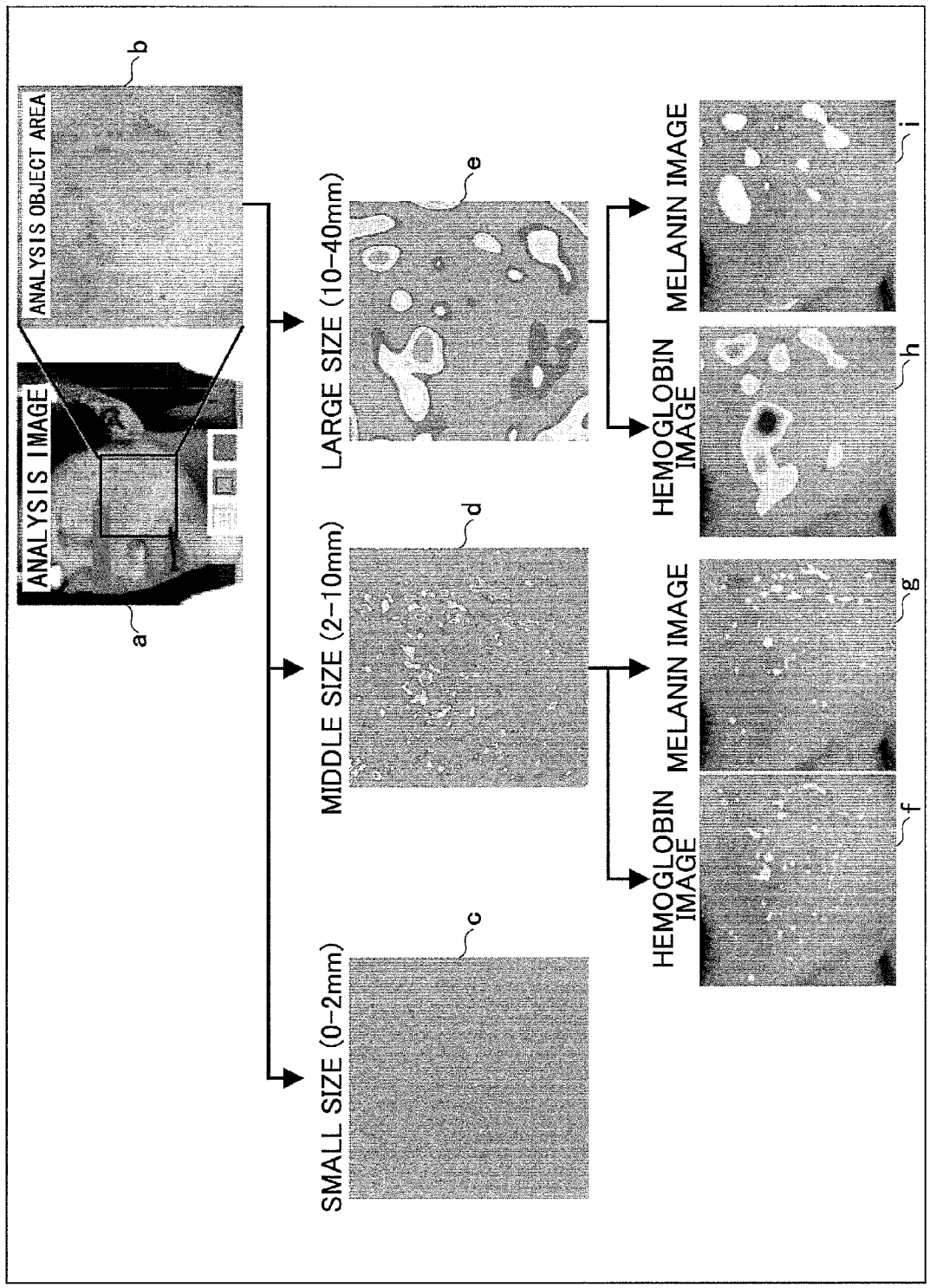
FIG. 5 is a view for explaining steps for obtaining a color heterogeneity index from the skin image.

Thus, as will foe explained in the following, the color heterogeneity are decomposed into a predetermined size, the decomposed color heterogeneity are digitized to obtain a color heterogeneity index, and a correlation relationship between the skin dullness and the color heterogeneity is studied. FIG. 5 is a view for explaining steps for obtaining the color heterogeneity index from the skin image.

In this embodiment, the image obtaining unit 14 obtains an image "a" of skin at a cheek portion of a subject photographed by using a diffused illumination box, a digital camera and the like, for example. Here, the obtained image of skin may include a wide range of a cheek portion from the side of nose to the side of ear of the subject as an analysis object area "b", and the image may be obtained in which dark rings under eyes, wrinkles around eyes, nasolabial folds or the like of the subject are removed.

Next, the frequency analysing unit 15 decompose the analysis object area "b" of the image obtained by the image obtaining unit 14 as an original image (skin image) into color heterogeneity of a predetermined size and obtains images "c" to "e" each of which is decomposed into color sports of a predetermined size. Specifically, the frequency analyzing unit 15 obtains the image "c" which is obtained by extracting color heterogeneity of small size whose half width is about from 0 to 2 mm, the image "d" which is obtained by extracting color heterogeneity of middle size whose half width is about from 2 to 10 mm, and the image "e" which is obtained by extracting color heterogeneity of large size whose half width is about 10 to 40 mm, by using a band-pass filter having a predetermined frequency or the like.

Next, the color heterogeneity index obtaining unit 16 obtains color data of skin for each of the image "c" in which the small size color heterogeneity are extracted, the image "d" in which the middle size color heterogeneity are extracted and the image "e" in which the large size color heterogeneity are extracted, by the frequency analyzing unit 15.

The color heterogeneity index obtaining unit 16, for example, multiplies, from density of the pigment composition and its distribution that are obtained based on the color data of skin of each of the images, a density value greater than or equal to a density average value and the number of pixels each of which having the density value greater than or equal to the density average value and integrates the multiplied value to obtain the color heterogeneity index. Here, the frequency analysing unit 15 and the color heterogeneity index obtaining unit 16 may use a method disclosed in Japanese Laid-open Patent Publication No. 2011-240086 by the present applicant, fox example.

Further, it is also possible to decompose into a melanin component and a hemoglobin component in skin and obtain the component amount of each of them using a method disclosed in Japanese Patent No. 3,798,550 by the present applicant, for example, (Involvement of Color Heterogeneity to Skin Dullness)

Figure 6:
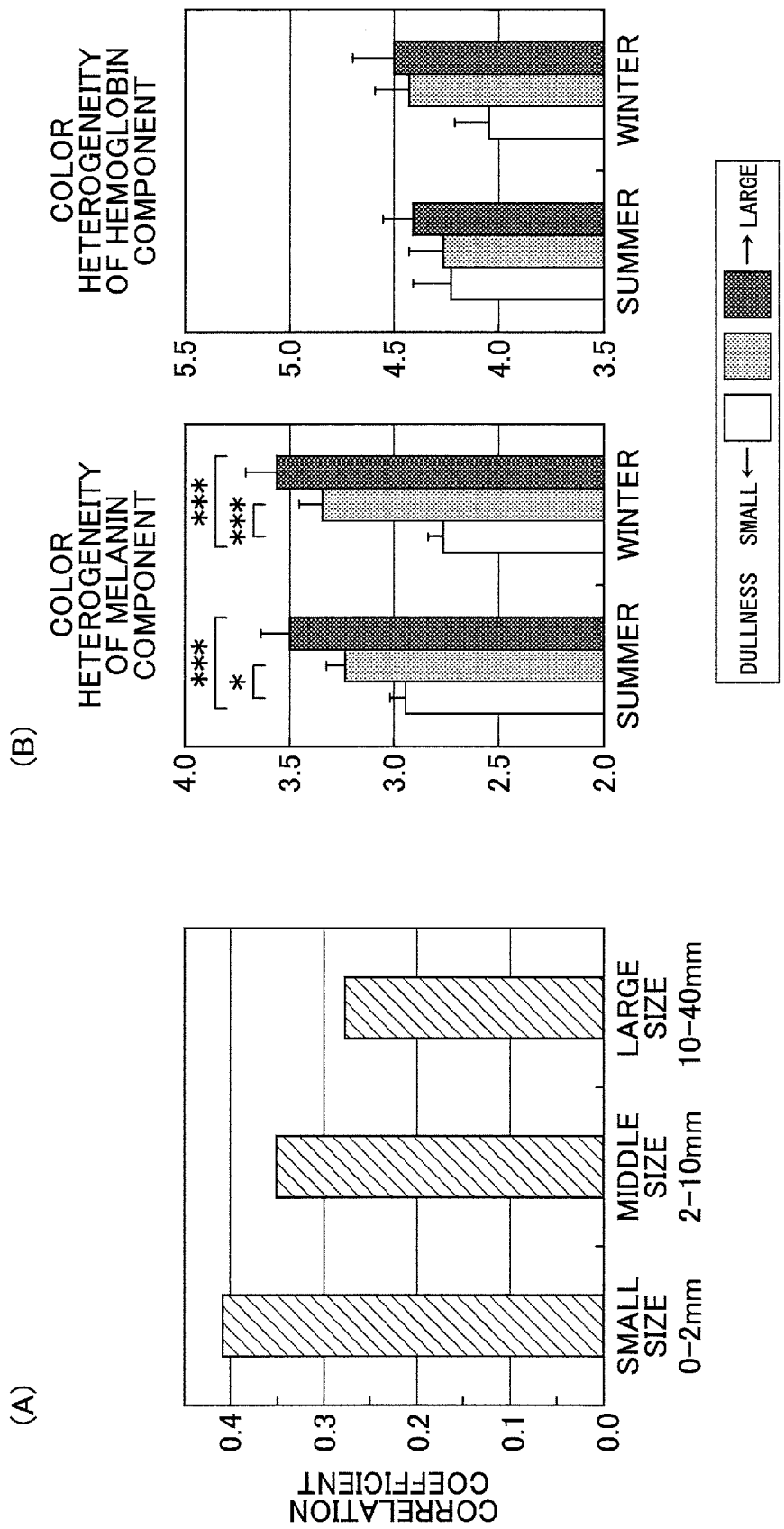
FIG. 6 is a view illustrating an example of a correlation relationship between the skin dullness and color heterogeneity.

FIG. 6-(A) and FIG. 6-(B) are views illustrating an example of a correlation relationship between the skin dullness and the color heterogeneity. FIG. 6-(A) illustrates an example of a correlation relationship between the skin dullness and the color heterogeneity of each size, and FIG. 6-(B) illustrates an example of a correlation relationship between the skin dullness and a pigment composition of the color heterogeneity.

FIG. 6-(A) is a view illustrating a correlation coefficient between an average value of a visual evaluation and the color heterogeneity index of each of the sizes digitized by the steps explained above with reference to FIG. 5-(B). In the visual evaluation, targeting 124 subjects, degree of the skin dullness was judged by 5 grades (from "not distinguishable" to "distinguishable") by four sensory evaluators, respectively.

With reference to FIG. 6-(A), the correlation coefficient between the skin dullness becomes larger as the size of the color heterogeneity becomes smaller, among the small size color heterogeneity, the middle size color heterogeneity and the large size color heterogeneity. In other words, it is indicated that the small size color heterogeneity influence on the skin dullness.

FIG. 6-(B) is a view illustrating an example of a correlation coefficient between the average value of the visual evaluation, similarly targeting 124 subjects, and the color heterogeneity index of small size for each of the pigment compositions digitized by the steps explained above with reference to FIG. 5-(B), respectively. With reference to FIG. 6-(B), for the color heterogeneity of the hemoglobin component, there is no difference between the values of the correlation coefficient regarding the skin dullness. On the other hand, for the color heterogeneity of the melanin component, there is a significant difference between the values of the correlation coefficient regarding the skin dullness. In other words, it is indicated that the color heterogeneity of the melanin component influence on the skin dullness.

Figure 7:
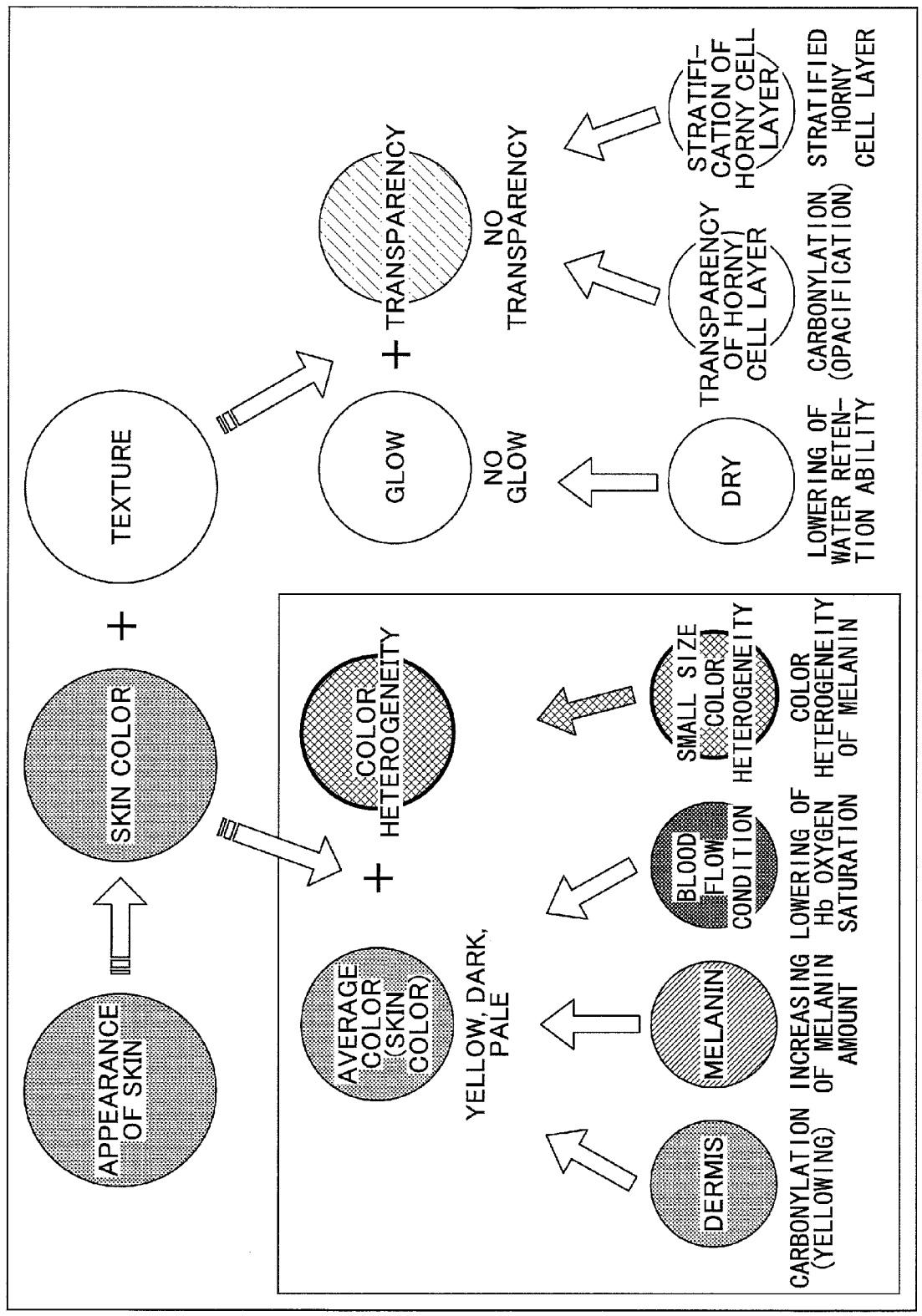
FIG. 7 is a schematic view in which color heterogeneity are added to the definition of the skin dullness.

FIG. 7 is a schematic view in which a concept of the color heterogeneity is added to the definition of the skin dullness. As described above, the skin dullness includes small size color heterogeneity and color heterogeneity of the melanin component influence on the skin dullness, for example. Thus, the definition of the skin dullness in which the concept of color heterogeneity is newly added to the conventional definition of the skin dullness is schematically explained.

As illustrated in FIG. 7, the skin dullness is explained by branching from the appearance of skin to "skin color" and "skin texture".

For example, when the skin dullness is explained by the "skin texture", if the skin dries due to the lowering of water retention ability, the feature of skin becomes a "no glow" condition, and the feature of skin becomes a "no transparency" condition due to the carbonylation (opacification) of a horny ceil layer and stratification of the horny cell layer.

Further, when the skin dullness is explained by the "skin color", the feature of skin becomes a condition in which the average color (skin color) is yellow, dark, and pale due to carbonylation (yellowing) of dermis, increasing of a melanin amount, lowering of Hb oxygen saturation which expresses a blood flow condition. Further, as illustrated in FIG. 7, the skin dullness can be explained such that the feature of skin becomes a condition in which color heterogeneity are generated due to the generation of small size color heterogeneity of the melanin component, for example.

(Influence of Size of Color Heterogeneity on Skin Dullness)

Figure 8:
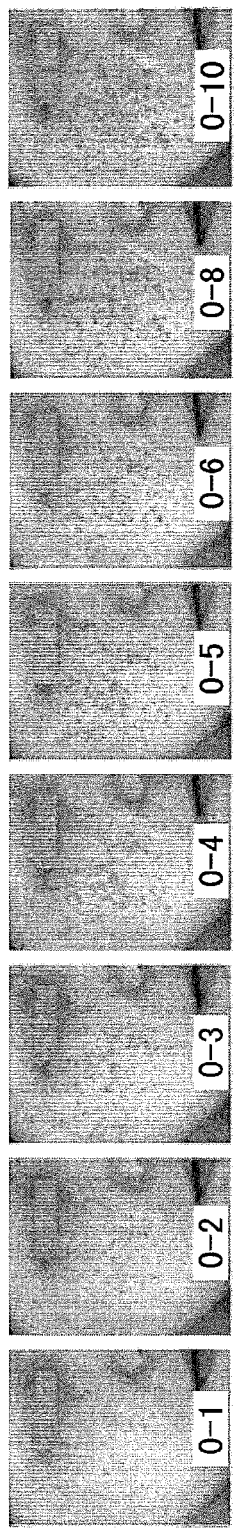
FIG. 8 is a view for explaining the influence of sizes of the color heterogeneity regarding the skin dullness.
Figure 8:
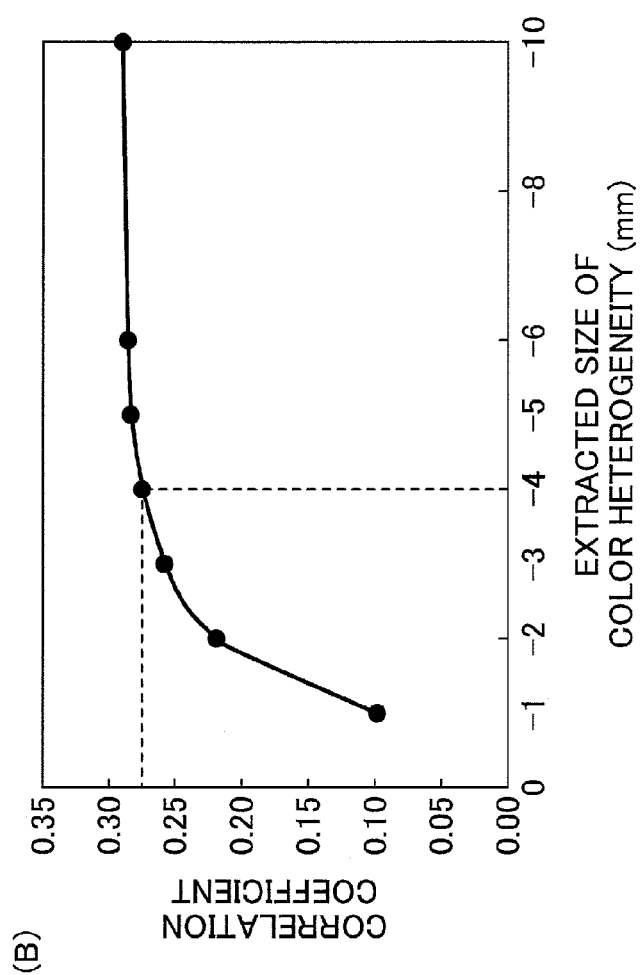

FIG. 8-(A) and FIG. 8-(B) are views for explaining the influence of the size of the color heterogeneity on the skin dullness. In the above explained examples of FIG. 6-(A) and FIG. 6-(B), it is indicated that the small size color heterogeneity influence on the skin dullness, and which size of the color heterogeneity influences the skin dullness is specifically analyzed.

In FIG. 8-(A), an example is illustrated in which color heterogeneity of stepwisely altered sizes (0 to 1 mm, 0 to 2 mm, . . . 0 to 10 mm) were extracted, and 8 patterns of color heterogeneity indexes were obtained for one subject by the above described steps illustrated in FIG. 5-(B). Here, "0 to 1 mm" means color heterogeneity each of which is less than or equal to 1 mm. This is the same for other values. Here, the color heterogeneity index may be obtained by "density" x "area" of color heterogeneity (integrated value of color difference $\Delta E$ of each pixel of the extracted color heterogeneity), for example.

Here, those 8 patterns of color heterogeneity indexes are obtained from each of the above described 124 subjects, and the correlation coefficient is obtained using the obtained color heterogeneity indexes and the average value of the visual evaluation by the 4 sensory evaluators for each of the subjects, similarly as FIG. 6-(A) and FIG. 6-(B), respectively.

FIG. 8-(B) illustrates correlation coefficient values between the skin dullness and the 8 patterns of the extracted sizes of the color heterogeneity. With reference to FIG. 8(B), the correlation coefficient values with the skin dullness of the extracted sizes of the color heterogeneity increases as the extracted size of the color heterogeneity increases among 0 to 4 mm, for example. On the other hand, when the extracted size of the color heterogeneity becomes larger than 4 mm, the correlation coefficient values with the skin dullness become substantially constant.

Thus, it is indicated that the relationship between the large size color heterogeneity larger than 4 mm, for example, and the skin dullness does not change almost not at all, and the color heterogeneity of 0 to 4 mm size influence on the skin dullness. As such, as the color heterogeneity of 0 to 4 mm size, for example, influence on the skin dullness, it is explained by referring such color heterogeneity to as "dullness color heterogeneity", for example.

(Examples of Extracting Color Heterogeneity of Size that Influence on Skin Dullness)

Figure 9:
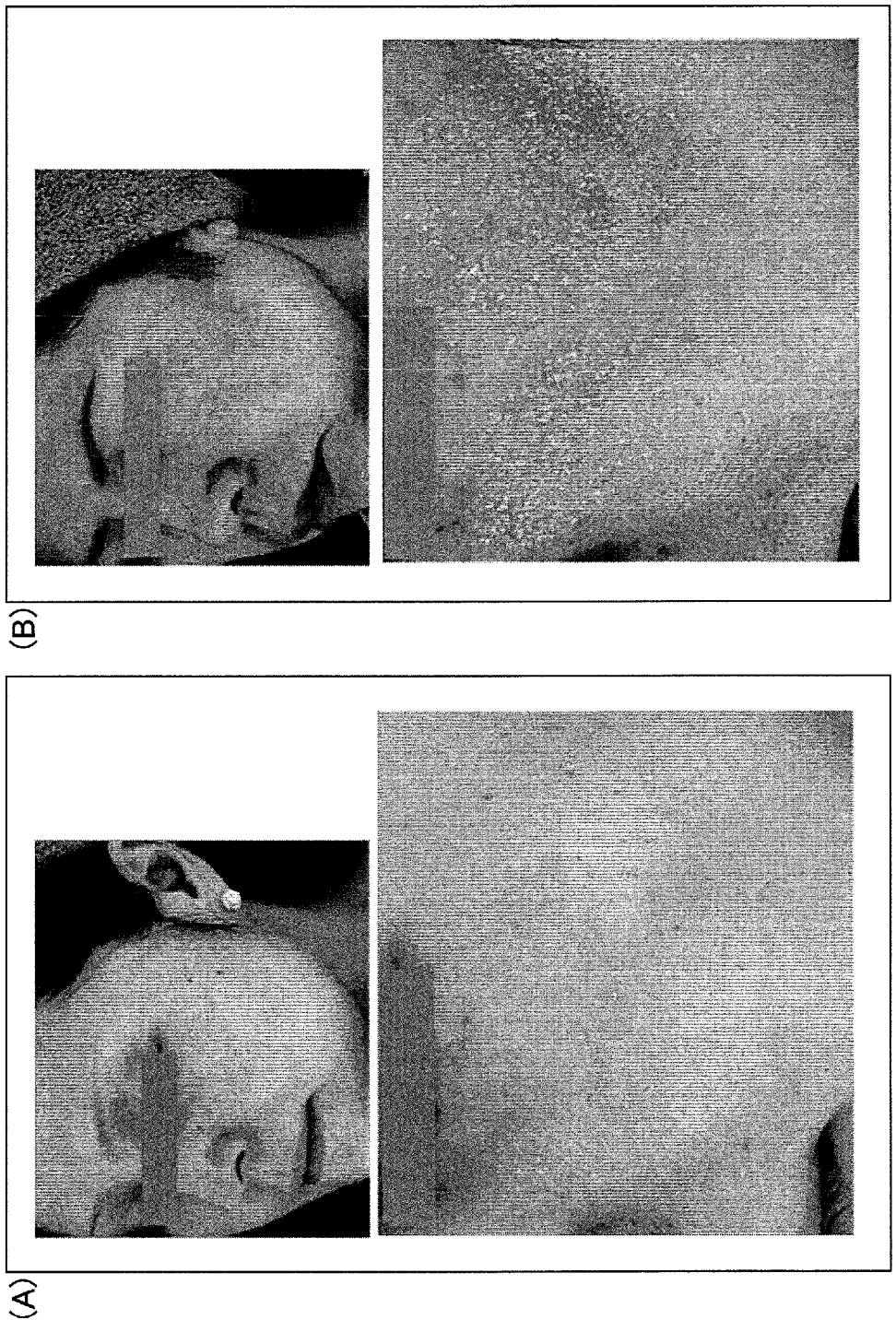
FIG. 9 is a view illustrating an example in which color heterogeneity of sizes that influence on the skin dullness are extracted.

FIG. 9-(A) and FIG. 9-(B) are views illustrating examples in which color heterogeneity having sizes that influence on the skin dullness are extracted. Here, FIG. 9-(A) illustrates an example of skin which is judged to have high transparency, and FIG. 9-(B) illustrates an example of skin which is judged that the skin dullness is distinguishable.

Here, dullness color heterogeneity (color heterogeneity of 0 to 4 mm) are extracted from each of the skin images illustrated in FIG. 9-(A) and FIG. 9-(B), and the color heterogeneity index is obtained by the steps illustrated in FIG. 5-(B), or by "density" x "area" of color heterogeneity (integrated value of color difference ΔE of each pixel of the extracted color heterogeneity).

While for the skin whose transparency is high as illustrated in FIG. 9-(A), the color heterogeneity index of the dullness color heterogeneity obtained as described above was "22.9", for the skin whose skin dullness was distinguishable as illustrated in FIG. 9-(B), the color heterogeneity index of the dullness color heterogeneity was "52.4".

As such, there is a clear difference between color heterogeneity index values obtained by digitizing the color heterogeneity having sizes that influence on the skin dullness for the skin whose transparency is high and the skin for which the dullness is distinguishable. Thus, in this embodiment, it is possible to evaluate the skin dullness using the value of the color heterogeneity index that is obtained by digitizing the dullness color heterogeneity, for example.

(Evaluation Method of Skin Color that is Defined as Skin Dullness)

Figure 10:
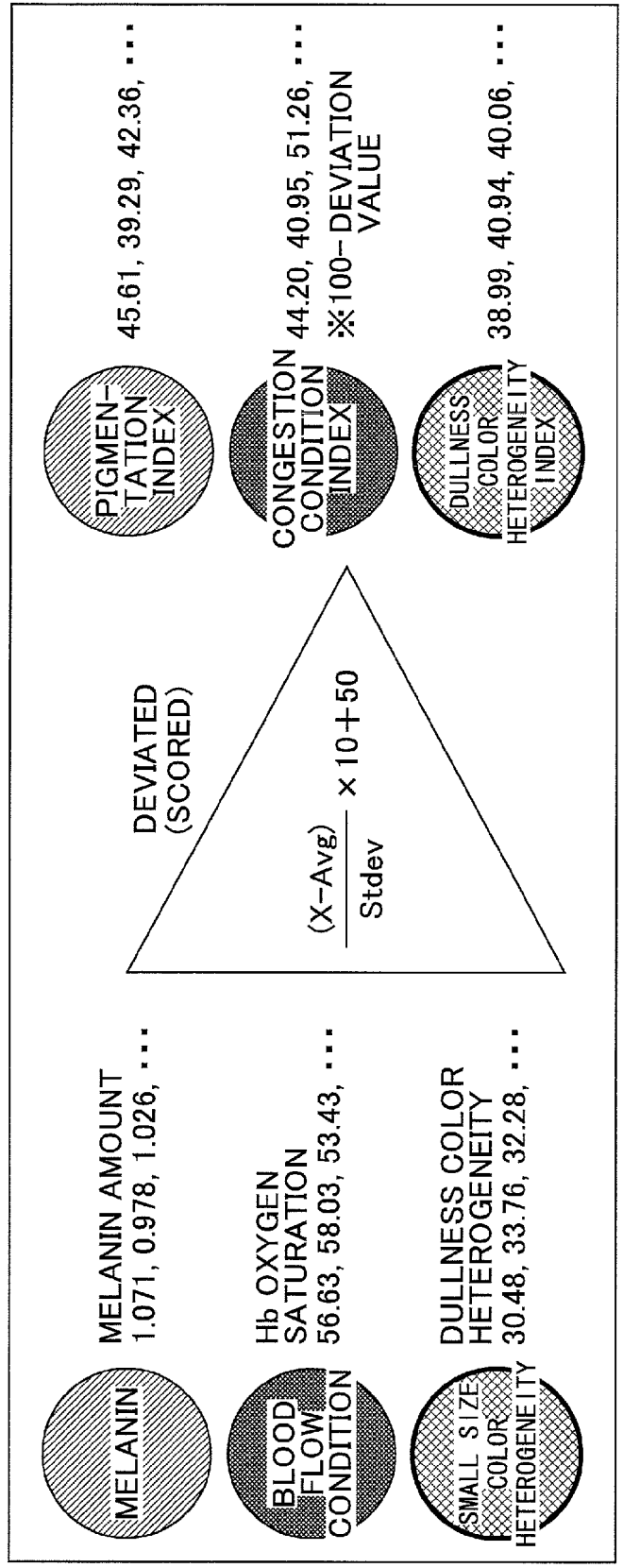
FIG. 10 is a view for explaining an evaluation method of skin color that is defined as the skin dullness.

FIG. 10 is a view for explaining an evaluating method of skin color that is defined as the skin dullness. As explained above with reference to FIG. 7, the skin color that is defined as the skin dullness is influenced by small size color heterogeneity of the melanin component or the like, in addition to carbonylation of dermis, increasing of the melanin amount, lowering of the Kb oxygen saturation indicating the blood flow condition.

Thus, as illustrated in FIG. 10, it is possible to evaluate the skin dullness by evaluating the skin color by values obtained by digitizing the skin color that is defined as the skin dullness, for example. In this embodiment, among factors that influence on the skin color, "melanin amount", "Hb oxygen saturation" indicating the blood flow condition and "dullness color heterogeneity" are used to digitize skin color, for example.

Here, the "melanin amount" and the "Hb oxygen saturation" may be obtained by measuring color of the skin image or the portion of skin corresponding to the skin image, for example. Further, as illustrated in above described FIG. 9-(A) and FIG. 9-(8), color heterogeneity of 0 to 4 mm size are extracted and the "dullness color heterogeneity index" that is obtained by digitizing the extracted color heterogeneity is used as the "dullness color heterogeneity".

Further, the "melanin amount", the "Hb oxygen saturation", and the "color heterogeneity index" are deviated (scored) and the scored values are used. For example, for the "melanin amount", the scored value is used as the "pigmentation index". The "Hb oxygen saturation" expresses the blood flow condition. Here, in order to obtain a value of a congestion condition as the skin dullness, a "congestion condition index" indicating a value of the congestion condition is used as the "Hb oxygen saturation" that is obtained by subtracting the scored value of the "Hb oxygen saturation" from a predetermined value (100, for example). As the "dullness color heterogeneity", the scored value of the color heterogeneity index is used as the "dullness color heterogeneity index".

For the example of FIG. 10, values are scored using (X−Ave)/Stdev×10+50, for example. With this, when the "melanin amount" is 1.071, 45.61 is obtained as the "pigmentation index", for example. When the "Hb oxygen saturation" is 56.63, 44.20 is obtained as the "congestion condition index", for example. Further, when the "dullness color heterogeneity" is 30.48, 38.99 is obtained as the "dullness color heterogeneity index".

Here, the skin color index obtaining unit 17 obtains the "pigmentation index", the "congestion condition index" and the "dullness color heterogeneity index"obtained as described above as the "skin color indexes" that axe digitized skin color.

(For Dullness Index)

Figure 11:
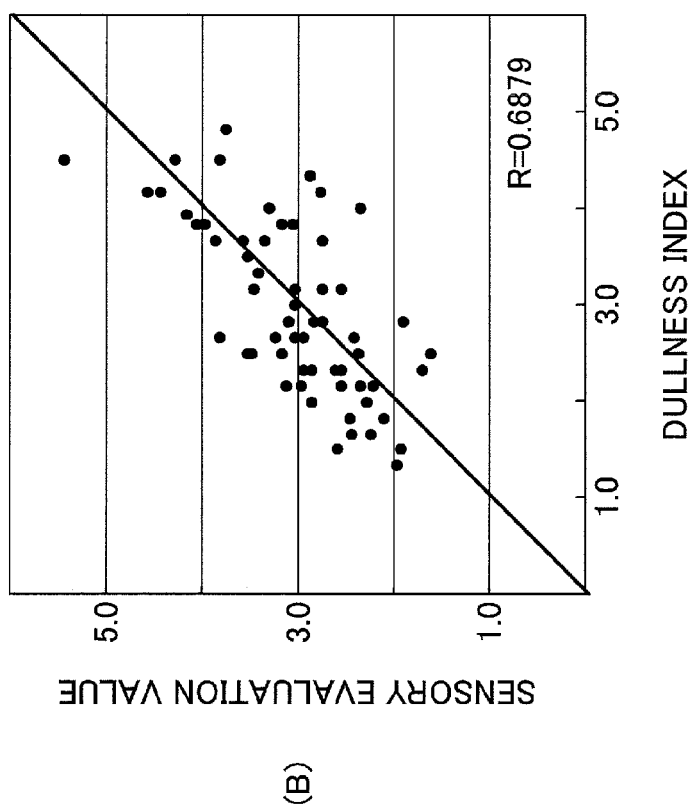
FIG. 11 is a view for explaining a dullness index.

FIG. 11-(A) and FIG. 11-(B) are views for explaining a dullness index. FIG. 11-(A) illustrates an example of a dullness index estimated formula, and FIG. 11-(B) is a view illustrating a relationship between the dullness index and a sensory evaluation value.

In order to evaluate the above described skin color that is defined as the skin dullness, the dullness index is obtained as follows using the skin color indexes (the pigmentation index, the congestion condition index, the dullness color heterogeneity index). The dullness index estimated formula illustrated in FIG. 11-(A) is obtained by performing a multiple regression analysis of function values setting each of the values of the pigmentation index, the congestion condition index and the dullness color heterogeneity index obtained by the measured data of the above described 124 subjects as explanatory variables and the sensory evaluation value (dependent variable), obtaining coefficient of each of the explanatory variables and determining the function.

FIG. 11-(B) illustrates an example of a result obtained by obtaining measured data of 61 subjects and verifying the dullness index obtained by inputting the pigmentation index, the congestion condition index and the dullness color heterogeneity index in the dullness index estimated formula illustrated in FIG. 11-(A), For the example illustrated in FIG. 11-(B), high correlation coefficient of 0.6879 was obtained by corresponding the dullness indexes of 61 subjects and the average values of the visual evaluation of degree of the skin dullness judged by 5 grades ("not distinguishable" to "distinguishable") by 3 sensory evaluators.

Thus, it is possible to evaluate the skin color that is defined as the skin dullness using the dullness index obtained by the above described dullness index estimated formula illustrated in FIG. 11-(A), and evaluate the skin dullness based on this.

(Process of Obtaining Dullness Index)

Figure 12:
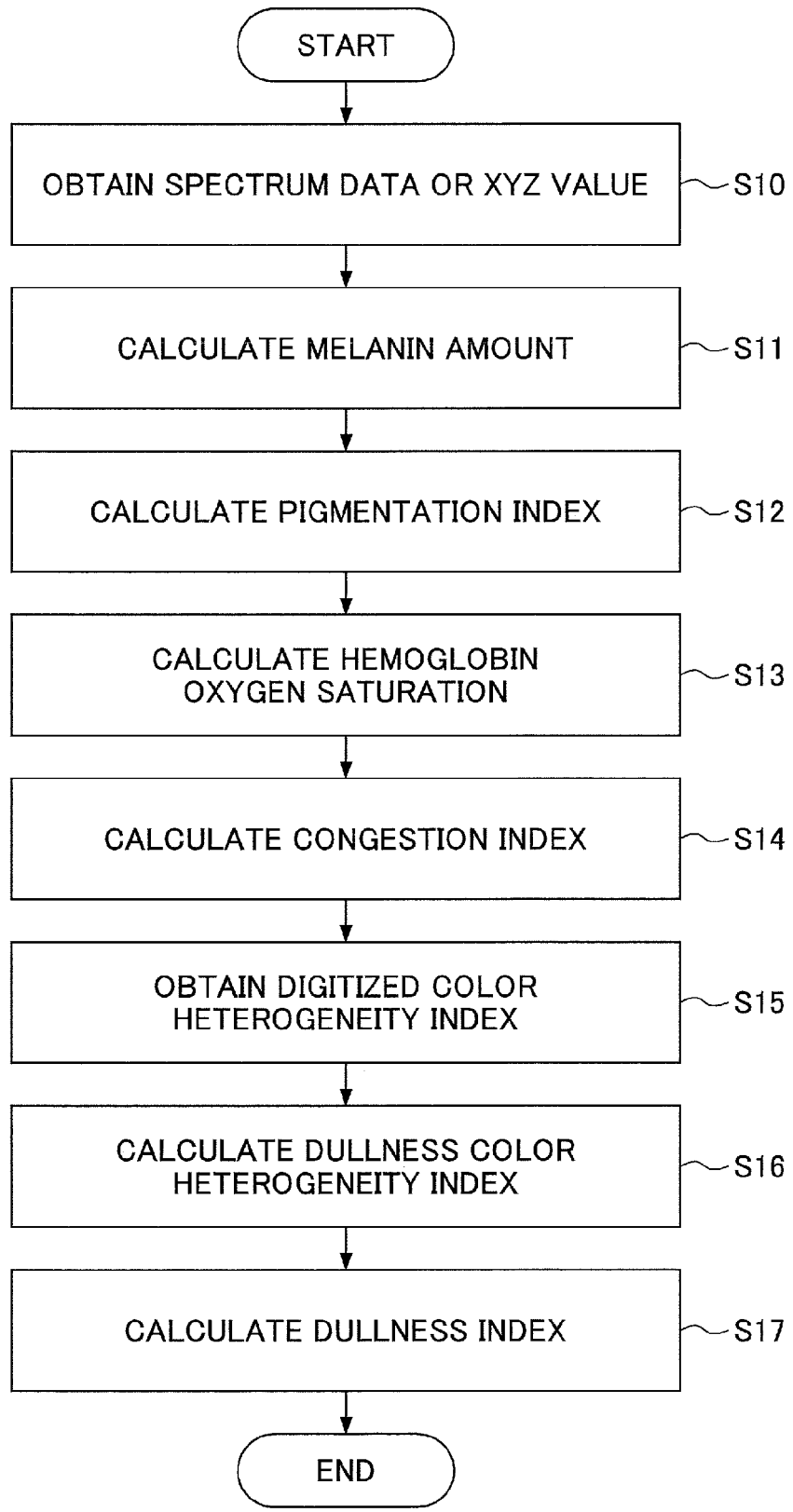
FIG. 12 is a flowchart illustrating a flow of processes for obtaining a skin dullness index.

FIG. 12 is a flowchart illustrating a flow of a process of obtaining the skin dullness index.

As illustrated in FIG. 12, upon obtaining reflection spectrum data obtained by measuring the color of skin, or an XYZ value from a skin image (S10), the skin color index obtaining unit 17 calculates the melanin amount (the component amount of the melanin component) from the obtained data or the like (S11), and obtains the "pigmentation index" by scoring the calculated melanin amount (S12).

Next, upon obtaining the Hb oxygen saturation (S13), the skin color index obtaining unit 17 obtains the "congestion condition index" indicating the congestion condition (S14).

Here, in the processes of S11 and S13, the melanin amount and the Hb oxygen saturation may be obtained by using methods disclosed in Japanese Patent No. 3,798,550 or Japanese Patent No. 3,727,807 by the present applicant, respectively.

Next, upon obtaining the color heterogeneity index from the color heterogeneity index obtaining unit 16 (S15), the skin color index obtaining unit 17 obtains the "dullness color heterogeneity index" (S16).

Next, the skin color index obtaining unit 17 calculates the dullness index by inputting the values obtained by the processes of S12, S14 and S16 to the dullness index estimated formula obtained by the multiple regression model (S17), for example, and ends the process.

(Specific Example of Dullness Judgment Value of Skin Color)

Figure 13:
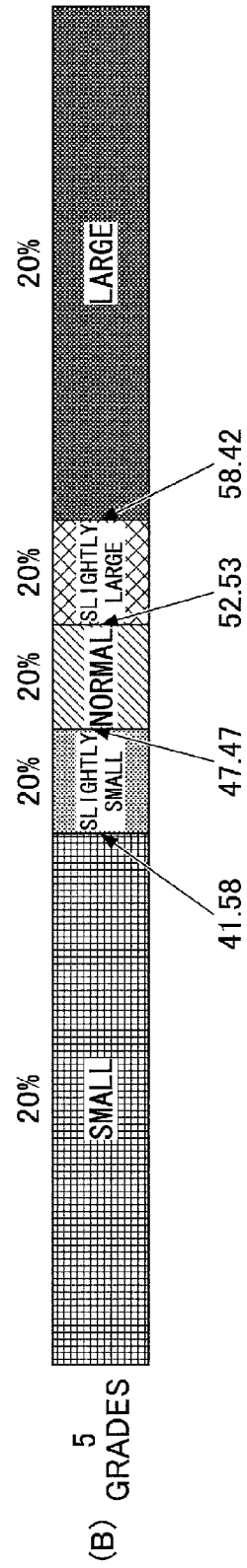
FIG. 13 is a view illustrating a specific example of a dullness judgment value of skin color.

FIG. 13-(A) and FIG. 13-(B) are views illustrating a specific example of a dullness judgment value of skin color. FIG. 13-(A) is an example of each index and a dullness judgment of skin color of each target to be evaluated, and FIG. 13-(B) illustrates an example of an evaluation criteria when evaluating each index by 5 grades.

In the example of FIG. 13-(A), an example is illustrated in which evaluation is performed to each target to be evaluated using items such as the "pigmentation index", the "congestion condition index", the "dullness color heterogeneity index", the "dullness index", the "dullness judgment value of skin color" or the like.

For example, for "female A", the pigmentation index is "T46.14", the congestion condition index is "T47.20", the dullness color heterogeneity index is "T38.11", the dullness index is "2.33", and the total dullness judgment value is "2 slightly weak".

For the evaluation criteria illustrated in FIG. 13-(B), in order to evaluate by 5 grades, for example, reference points are set for classifying the targets be evaluated to each grade such that each grade includes 20% using the scored value, where the targets are classified to "small", "slightly small", "normal", "slightly large" and "large". For example, in an example of FIG. 13-(B), the targets are classified to "small" and "slightly small" by setting the scored value "41.58" as a reference point. Further, the targets are classified to "slightly small" and "normal" by setting the scored value "47.47" as a reference point.

Here, it is possible for the dullness evaluation unit 18, using the evaluation criteria of FIG. 13-(B) for "female A" of FIG. 13-(A), to evaluate as "slightly small" using the pigmentation index "T46.14", "slightly small" using the congestion condition index "T47.20" or the like. Further, it is possible for the dullness evaluation unit 18 to evaluate the skin dullness by judging the total dullness judgment value of skin color as "2 slightly weak" using the dullness index "2.33" obtained by the dullness index estimated formula, for example.

(Example of Dullness Judgment of Skin Color)

Figure 14:
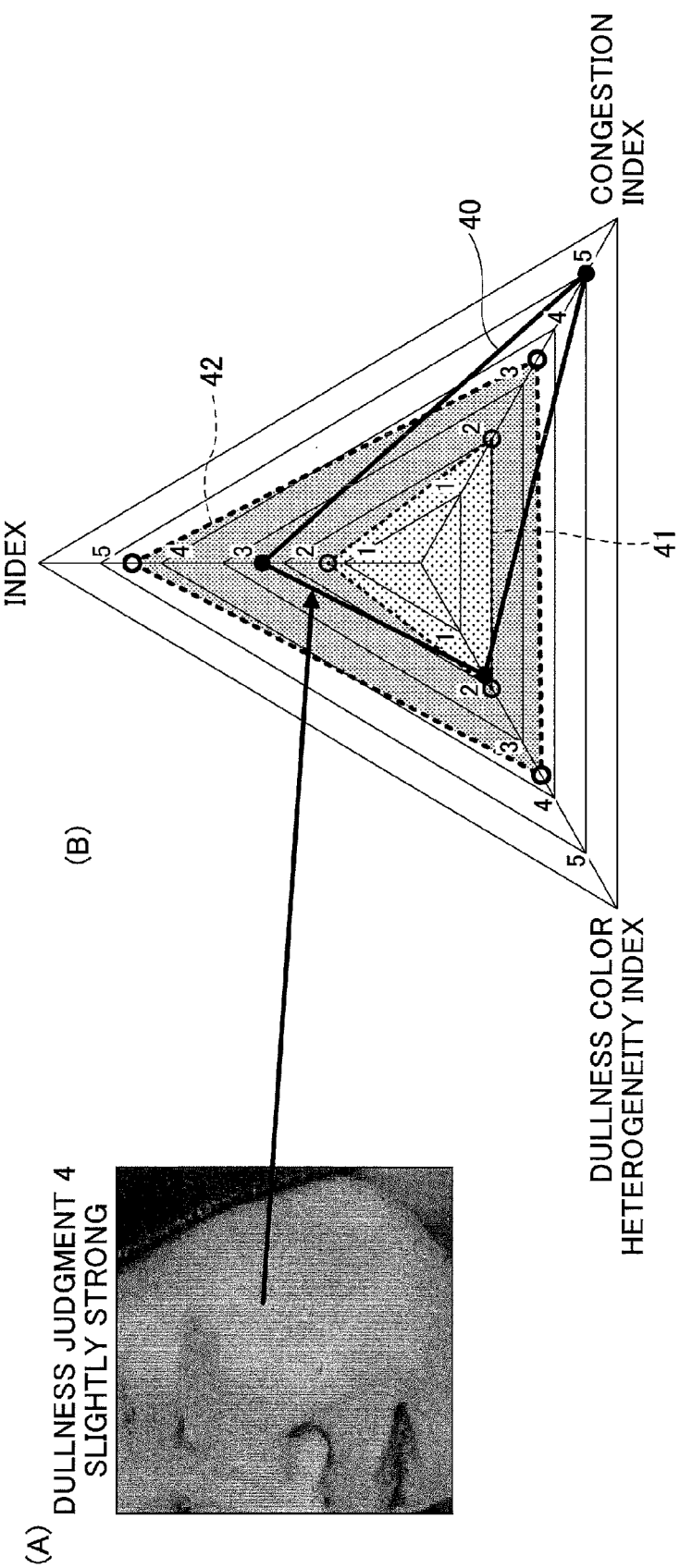
FIG. 14 is a view illustrating an example of a dullness judgment of skin color.

FIG. 14-(A) and FIG. 14-(B) are views illustrating an example of the dullness judgment of skin color. FIG. 14-(A) illustrates a skin image that is used for the dullness judgment of skin color, and FIG. 14-(B) illustrates the judgment values of the indexes of the skin image illustrated in FIG. 14-(A).

The skin image illustrated in FIG. 14-(A) illustrates an example for which the dullness judgment value is judged as "4 slightly strong" based on the above described indexes. For the example of the dullness judgment illustrated in FIG. 14-(B), the pigmentation index, the congestion condition index and the dullness color heterogeneity index are classified to 5 grades, respectively.

It is possible to illustrate a triangle 40 having the pigmentation index "2.6", the congestion condition index "5" and the dullness color heterogeneity index "2" as vertexes thereof when expressing the indexes of the skin image illustrated in FIG. 14-(A) on FIG. 14-(B). Here, a triangle 41 illustrated in FIG. 14-(8) indicates average data of skins that are judged to have transparency, and a triangle 42 illustrated in FIG. 14-(B) indicates average data of skins that are judged to have the dullness.

As such, it is possible to evaluate the skin dullness by judging the total dullness of skin color using the indexes. Further, it is possible to illustrate which factor influences largely or the like by illustrating which index value is high for the dullness of skin color.

As described above, according to the embodiment, it is possible to appropriately evaluate the skin dullness using color heterogeneity.

Although a preferred embodiment of the invention has been specifically illustrated and described, it is to be understood that minor modifications may be made therein without departing from the spirit and scope of the invention as defined by the claims.

The present application is based on and claims the benefit of priority of Japanese Priority Application No. 2013-094131 filed on Apr. 26, 2013, the entire contents of which are hereby incorporated by reference.

NUMERALS

10 dullness evaluation apparatus
11 input unit
12 output unit
13 storing unit
14 image obtaining unit
15 frequency analyzing unit
16 color heterogeneity index obtaining unit
17 skin color index obtaining unit
18 dullness evaluation unit
19 control unit
31 input device
32 output device
33 drive device
34 auxiliary storage
35 memory device
36 CPU
37 network connection device
38 recording medium

What is claimed is:

1. A skin dullness evaluation apparatus comprising:
a frequency analyzing unit that decomposes a skin image into color heterogeneity of a predetermined size;
a color heterogeneity index obtaining unit that obtains color data of skin from each of the color heterogeneity decomposed by the frequency analysing unit, and obtains a color heterogeneity index of the color heterogeneity from the obtained color data of skin; and
a dullness evaluation unit that evaluates skin dullness corresponding to the skin image based on the color heterogeneity index obtained by the color heterogeneity index obtaining unit.

2. The skin dullness evaluation apparatus according to claim 1,
wherein the frequency analyzing unit decomposes the skin image into color heterogeneity of less than or equal to 4 mm as the predetermined size.

3. The skin dullness evaluation apparatus according to claim 1,
wherein the color heterogeneity index obtaining unit obtains the color heterogeneity index based on distribution of a predetermined pigment composition obtained from the color data of skin.

4. The skin dullness evaluation apparatus according to claim 3,
wherein the predetermined pigment composition is a melanin component.

5. The skin dullness evaluation apparatus according to claim 1, further comprising:
a skin color index obtaining unit that obtains a skin color index based on color data of skin obtained from the skin image or a portion of skin corresponding to the skin image,
wherein the dullness evaluation unit evaluates the skin dullness corresponding to the skin image based on the skin color index obtained by the skin color index obtaining unit.

6. The skin dullness evaluation apparatus according to claim 5,
wherein the skin color index obtaining unit obtains, as the skin color index, a pigmentation index based on a component amount of a melanin component, a congestion condition index based on hemoglobin oxygen saturation or a dullness color heterogeneity index based on the color heterogeneity index.

7. The skin dullness evaluation apparatus according to claim 6,
wherein the dullness evaluation unit evaluates the skin dullness corresponding to the skin image based on a skin dullness index obtained by performing a multiple regression analysis using the dullness color heterogeneity index, the pigmentation index and the congestion condition index.

8. A skin dullness evaluation method executed by a computer, the method comprising:
a frequency analyzing step of decomposing a skin image into color heterogeneity of a predetermined size;
a color heterogeneity index obtaining step of obtaining color data of skin from each of the color heterogeneity decomposed in the frequency analyzing step, and obtaining a color heterogeneity index of the color heterogeneity from the obtained color data of skin; and
a dullness evaluation step of evaluating skin dullness corresponding to the skin image based on the color heterogeneity index obtained in the color heterogeneity index obtaining step.

9. The skin dullness evaluation method according to claim 8,
wherein in the frequency analyzing step, the skin image is decomposed into color heterogeneity of less than or equal to 4 mm as the predetermined size.

10. The skin dullness evaluation method according to claim 8,
wherein in the color heterogeneity index obtaining step, the color heterogeneity index is obtained based on distribution of a predetermined pigment composition obtained from the color data of skin.

11. The skin dullness evaluation method according to claim 10,
wherein the predetermined pigment composition is a melanin component.

12. The skin, dullness evaluation method according to claim 8, further comprising:
a skin color index obtaining step of obtaining a skin color index based on color data of skin obtained from, the skin image or a portion of skin corresponding to the skin image,
wherein in the skin dullness evaluation step, the skin dullness corresponding to the skin image is evaluated based on the skin color index obtained in the skin color index obtaining step.

13. The skin dullness evaluation method according to claim 12,
wherein the skin color index obtaining step, as the skin color index, a pigmentation index based on a component amount of a melanin component, a congestion condition index based on hemoglobin oxygen saturation or a dullness color heterogeneity index based on the color heterogeneity index.

14. The skin dullness evaluation method according to claim 13,
wherein in the dullness evaluation step, the skin dullness corresponding to the skin image is evaluated based on a skin dullness index obtained by performing a multiple regression analysis using the dullness color heterogeneity index, the pigmentation index and the congestion condition index.

15. A non-transitory computer-readable recording medium having recorded there on a skin dullness evaluation program that causes a computer to function as units included by the dullness evaluation apparatus according to claim 1.

* * * * *